(12) United States Patent
Owens et al.

(10) Patent No.: US 6,669,937 B2
(45) Date of Patent: Dec. 30, 2003

(54) MONOCLONAL ANTIBODY ANTAGONISTS FOR TREATING MEDICAL PROBLEMS ASSOCIATED WITH D-AMPHETAMINE-LIKE DRUGS

(75) Inventors: Samuel M. Owens, Little Rock, AR (US); Frank Ivy Carroll, Durham, NC (US); Philip Abraham, Cary, NC (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 205 days.

(21) Appl. No.: 09/839,549

(22) Filed: Apr. 20, 2001

(65) Prior Publication Data

US 2001/0051158 A1 Dec. 13, 2001

Related U.S. Application Data

(60) Provisional application No. 60/198,902, filed on Apr. 20, 2000.

(51) Int. Cl.[7] .................. A61K 39/395; C07K 16/44
(52) U.S. Cl. ................. 424/142.1; 424/141.1; 530/388.9; 530/389.8; 562/451
(58) Field of Search .................... 530/388.9, 389.8; 424/141.1, 142.1

(56) References Cited

U.S. PATENT DOCUMENTS

| | | | | |
|---|---|---|---|---|
| 4,329,281 A | * | 5/1982 | Christenson et al. | |
| 5,041,076 A | * | 8/1991 | Kantor | |
| 5,135,863 A | * | 8/1992 | Hu et al. | |
| 5,238,652 A | * | 8/1993 | Sun et al. | |
| 5,492,841 A | * | 2/1996 | Craig | |
| 5,976,812 A | * | 11/1999 | Huber et al. | |
| 6,087,184 A | * | 7/2000 | Magginetti et al. | |
| 6,306,616 B1 | * | 10/2001 | Shindelman | |

FOREIGN PATENT DOCUMENTS

| | | | |
|---|---|---|---|
| EP | 343346 A1 | * | 11/1989 |
| EP | 574782 A2 | * | 12/1993 |
| WO | WO-92/03163 A1 | * | 3/1992 |
| WO | WO-97/49732 A1 | * | 12/1997 |

* cited by examiner

*Primary Examiner*—Mary E. Ceperley
(74) *Attorney, Agent, or Firm*—Benjamin Aaron Adler

(57) ABSTRACT

The invention includes synthetic immunochemical haptens for the generation of antibodies, the antibodies, and the medical treatment applications for using the antibodies. The antibodies are designed to recognize the common molecular features of d-methamphetamine-like abused stimulants, and will have insignificant cross-reactivity with endogenous substrates (e.g. dopamine) or over-the-counter medications (e.g. 1-methamphetamine, pseudoephedrine, phenylpropanolamine and ephedrine). These monoclonal antibodies and their antigen binding fragments are useful in treatment plans for recovering addicts, in emergency room settings for rapidly reversing a drug overdose, in protection of fetuses or fetus from drug-abusing pregnant mothers or in a psychiatric setting to reduce the exacerbation of psychotic disorders caused by stimulant drugs.

10 Claims, 13 Drawing Sheets

*d*-Amphetamine (+)Methamphetamine

MDMA

1

X = 2 to 9
connection at 2,
3, or 4 position

2

X = 1 to 6
connection at 2,
3, or 4 position

3

X = 1 to 6
connection at 2,
3, or 4 position

4

X = 2 to 4
Y = 1 to 5
connection at 2,
3, or 4 position

5

X = 2, 3
connection at 2,
3, or 4 position
R = alkyl 1-5 carbon

11

X = 3 to 8
connection at 2,
3, or 4 position

12

X = 2 to 7
connection at 2,
3, or 4 position

13

X = 2 to 7
connection at 2,
3, or 4 position

14

X = 1 to 6
connection at 2,
3, or 4 position

15

X = 1 to 6
connection at 2,
3, or 4 position

6

X = 2 to 9
connection at 2,
3, or 4 position

7

X = 1 to 6
connection at 2,
3, or 4 position

8

X = 1 to 6
connection at 2,
3, or 4 position

9

X = 2 to 4
Y = 1 to 5
connection at 2,
3, or 4 position

10

X = 2, 3
connection at 2,
3, or 4 position
R = alkyl 1-5 carbon a: (R)C$_6$H$_5$CH(NH$_2$)CH$_3$, toluene
b: Raney Ni/H$_2$
c: HCO$_2$H/Ac$_2$O
d: BBr$_3$
e: NaH/Br(CH$_2$)$_5$CO$_2$CH$_3$
f: BH$_3$
g: Pd/HCO$_2$H
h: Dilute HCl

MONOCLONAL ANTIBODY ANTAGONISTS FOR TREATING MEDICAL PROBLEMS ASSOCIATED WITH D-AMPHETAMINE-LIKE DRUGS

CROSS-REFERENCE TO RELATED APPLICATION

This non-provisional patent application claims benefit of provisional patent application U.S. Ser. No. 60/198,902, filed Apr. 20, 2000, now abandoned.

FEDERAL FUNDING

This invention was produced in part using funds obtained through grant number R01 DA11560 from the National Institute on Drug Abuse. Consequently, the federal government has certain rights in this invention.

BACKGROUND OF THE INVENTION

1. Field of the Invention

The present invention relates generally to the field of drug abuse and addiction therapy. More specifically, the present invent ion relates to the generation and use of high affinity monoclonal antibodies (MAb) and their derivatives as long acting stimulant antagonists for treating the medical problems associated with drug abuse and addiction. In addition, the antigen binding fragments (Fab) and other small molecular fragments of these monoclonal antibodies can serve as a shorter acting stimulant antagonist for treating medical problems like drug overdose.

2. Description of the Related Art

Knowledge gained from basic research into the neurobiology of drug abuse has led to major discoveries in medicine. Nevertheless, the development of medical strategies for treating the complex array of neurological problems associated with drug abuse has been frustratingly slow. In particular, development of medical treatments for alleviating the adverse psychosocial and health effects of d-methamphetamine and similar stimulants is badly needed.

d-Methamphetamine-related hospital emergency cases across the U.S. increased 256% from 1991 to 1994 (1). The 1995 Toxic Exposure Surveillance System data showed there were 7,601 people treated in health care facilities for amphetamine-like drugs and other stimulants. This is particularly striking since during the same period there were only 3,440 cases of cocaine treatment and a total of 5,170 cases of all types of legal and illegal narcotics (including morphine, codeine and heroin). The current rise in d-methamphetamine use is also alarming because, unlike cocaine, it does not have to be imported. Even an amateur chemist can synthesize this drug in his home using easily obtained reagents and equipment.

The adverse clinical effects from d-methamphetamine include hypertension, tachycardia, dysrhythmias, sleep deprivation, a stimulant-induced psychosis as well as hyper-locomotion and stereotyped behavior (2). The central nervous system (CNS) actions of d-methamphetamine result from its effects on several CNS neurotransmitter systems, ion channels, and presynaptic catecholamine uptake systems. In particular, d-methamphetamine has profound effects on the CNS dopaminergic system, where d-methamphetamine acts as a substrate for the dopamine transporter and causes dopamine to be transported extraneuronally which increases synaptic concentrations of dopamine (2). Indeed, d-methamphetamine can be transported into the presynaptic terminal without inhibiting reuptake of the neurotransmitter into the presynaptic terminal. These dopaminergic effects are associated with mood changes, excitation, motor movements and regulation of appetite.

There are no specific treatments (either as antagonists or as agonist replacement therapies) currently available for d-methamphetamine abuse. Therapy for drug overdose only involves medical management of the symptoms (e.g. hyperactivity, psychosis, and increased core body temperature) with palliative care until the drug effects subside, whereas therapy for helping patients gain control of their addiction mostly involves long term behavioral modification therapy and counseling without any significant useful medications.

One biologically based approach to treating drug overdose is the use of high-affinity, drug-specific Fab fragments of antibodies or intact IgG. In addition to being relatively safe, except for occasional allergic reactions that can be prevented by the use of human monoclonal antibodies, antibody-based therapies act as pharmacokinetic antagonists which gives them several important advantages over treatment with more conventional receptor antagonists. Firstly, there is no receptor antagonist for d-methamphetamine effects at any of its sites of action in the CNS. One of the limitations of development of receptor antagonists is that they will only be capable of attenuating the effects at one type of receptor. Most drugs of abuse have multiple sites of action. Secondly, unlike conventional receptor antagonists (or agonists), antibodies do not inhibit the actions of normal endogenous ligands. In fact, it could be argued that removal of the drug by antibodies might allow for a more normal recovery than treatment with a chemically-derived small molecule competitive agonist or antagonist. Thirdly, since antibodies (and their derivatives like Fab) have extremely high affinities and do not cross the blood-brain barrier, they actually lower drug concentrations throughout the CNS (3). This allows for a rapid, neuroprotective effect at all sites of action in the CNS.

The prior art is deficient in the lack of effective means of treating d-methamphetamine overdose and addiction. The present invention fulfills this long-standing need and desire in the art.

SUMMARY OF THE INVENTION

The present invention is drawn to the generation of high affinity monoclonal antibodies, and the use of intact and smaller derivatives of the antibody for treating the medical problems associated with stimulant drug abuse. D-Methamphetamine is the prototypic amphetamine-like drug molecule since it has severe addiction liability, and repeated use of the drug can lead to life-threatening cardiovascular problems, severe depression, psychosis, violent behavior and significant criminal activity. The antibodies are specifically designed to recognize the unique and/or common molecular features of several dangerous stimulant and hallucinogenic drugs of abuse and their psychoactive metabolites, e.g., d-methamphetamine, d-amphetamine, (+/−) 3,4-methylenedioxymethamphetamine (MDMA), and (+/−) 3,4-methylenedioxyamphetamine (MDA) or structurally related stimulants and/or hallucinogenic analogs.

In one embodiment of the present invention, there is provided a method to generate antibodies that are specifically designed to recognize the common molecular features of several dangerous stimulant and hallucinogenic drugs of abuse and their psychoactive metabolites chosen from the representative group consisting of d-methamphetamine, (+/−) 3,4-methylenedioxymethamphetamine, d-amphetamine, and (+/−) 3,4-methylenedioxyamphetamine or structually related stimulants and/or hallucinogenic analogs.

In another embodiment of the present invention, there is provided a series of haptens designed for generating class-specific monoclonal antibody that could be used as a pharmacokinetic antagonist for treating the medical problems associated with methamphetamine-like stimulants. There is also provided compounds used in coupling the hapten to a protein for generating the class-specific monoclonal antibody.

In another embodiment of the present invention, there is provided a method to directly compare active and passive immunization as treatments for d-methamphetamine addiction in rats.

In yet another embodiment of the present invention, there is provided a method to study the effect of anti-d-methamphetamine Fab on pharmacokinetics and behavior after stimulant-induced toxicity in rats.

In still yet another embodiment of the present invention, there is provided a method of antibody treatment in a preclinical model of human drug overdose.

In another aspect of the present invention, there is provided a method to assess d-methamphetamine self-administration in rats as a measure of the therapy's ability to reduce drug addiction liability.

The present invention is further drawn to a method to study the effect of antibody-based therapy on d-methamphetamine toxicity in dogs or primates.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the use of short-acting anti-methamphetamine monoclonal antibody fragment to treat an overdose resulting from d-amphetamine-like drugs. In this case d-methamphetamine is used as the prototype drug and an anti-methamphetamine monoclonal Fab is used as the antibody-based medication.

FIG. 2 shows the use of a long-acting anti-METH antibody medication for the treatment of drug addiction. In this clinical scenario, the patient has entered a drug treatment program for d-methamphetamine addiction and they are treated with a long acting anti-methamphetamine monoclonal antibody-based medication. In this example, the prototype long acting antagonist is an IgG antibody.

FIG. 8 shows the results from treatment of a methamphetamine-induced overdose in rats with a monoclonal anti-methamphetamine antibody. This proof of concept study shows anti-methamphetamine antibody therapy can significantly reduce d-methamphetamine toxicity compared to a saline or anti-phencyclidine monoclonal antibody treatment (a control monoclonal antibody that does not bind amphetamine like drugs). Rats (n=4 per group) were administered saline (left most bar) or 1.0 mg/kg d-methamphetamine as an intravenous bolus dose. When drug effects were maximizing at 30 minutes, they were treated with saline (control), an anti-phencyclidine monoclonal antibody Fab fragment (anti-PCP), or an anti-d-methamphetamine-specific monoclonal antibody Fab fragment (anti-methamphetamine).

FIG. 9 shows the use of anti-(+)METH monoclonal antibodies to reverse drug overdose and as a pretreatment to reduce drug effects.

DETAILED DESCRIPTION OF THE INVENTION

Figure 1A:
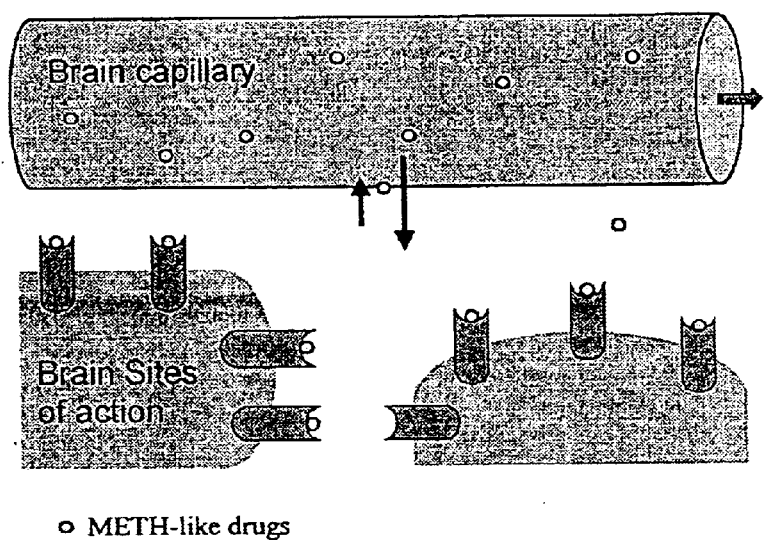
FIG. 1A shows that before the treatment with anti-METH antibody medication, the patient arrives in an emergency room with a high body burden of methamphetamine. This drawing shows that brain concentrations are very high and the drug is occupying drug sites of action in the patient's brain. This is producing the clinical overdose.
Figure 1B:
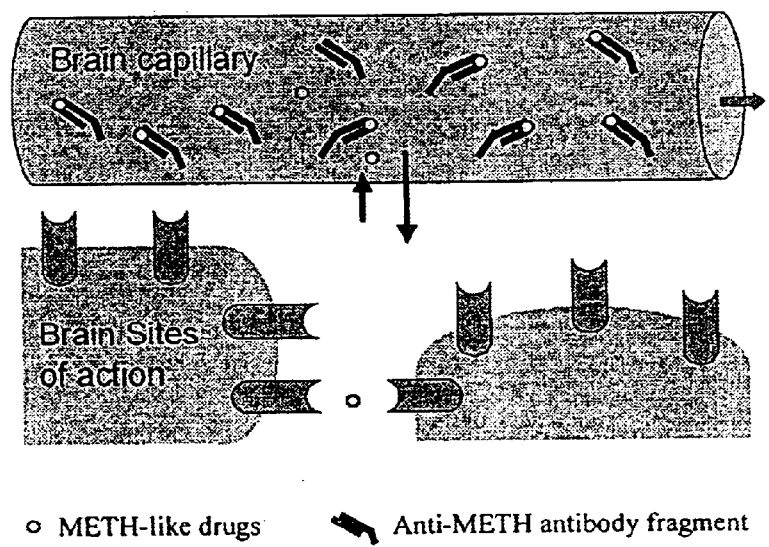
FIG. 1B shows after treatment with anti-methamphetamine antibody fragments, the drug is rapidly removed from the brain and the patient quickly recovers. In this example, the prototype short acting antibody based medication is anti-methamphetamine antibody fragments
Figure 2A:
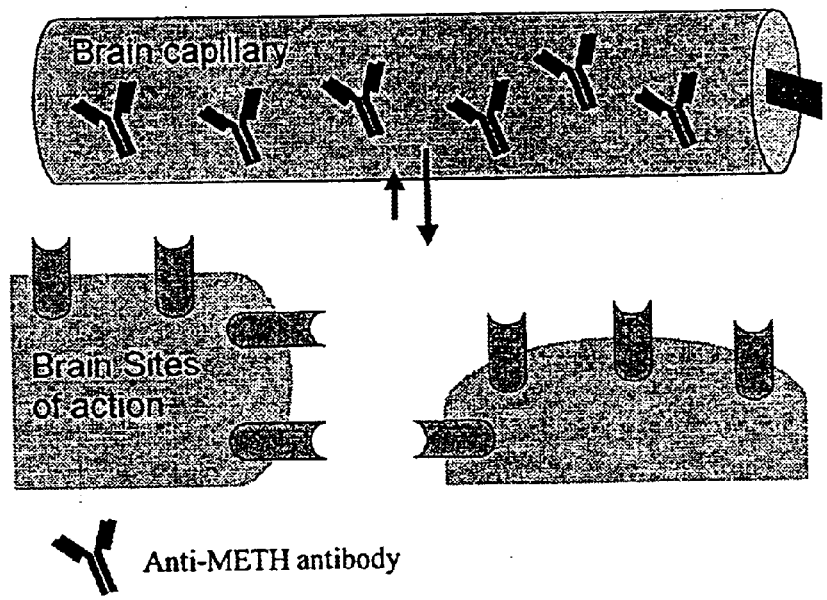
FIG. 2A shows the patient's brain after receiving a dose of a long-acting anti-METH antibody when they enter into a drug treatment program. This medication will serve as a treatment to help prevent or blunt the rewarding effects of amphetamine-like drug usage by the recovering addict.
Figure 2B:
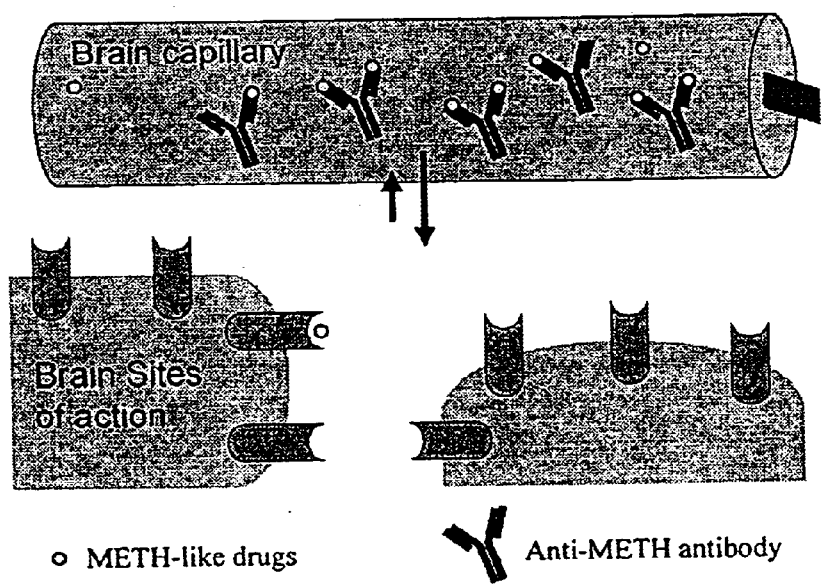
FIG. 2B shows after the patient is pre-treated with the anti-methamphetamine antibody medication, accidental or purposeful use of d-amphetamine-like drugs by the patient will be blocked or at least significantly blunted. Thus, the drug(s) can not reach their site of action in the central nervous system. This will prevent the patient from feeling the reinforcing effects of drug use, and aid in the prevention of relapse.

As used herein, the term "monoclonal antibody" means an antibody composition recognizing a discrete antigen determinant. It is not intended to be limited with regard to the source of the antibody or the manner in which it is made. The term antibody is also intended to encompass whole antibodies, biologically functional fragments thereof, chimeric and humanized antibodies comprising portions from more than one species, or other molecules whose binding properties are derived from antibody-like high affinity binding sites.

In this instance, monoclonal antibodies have been produced by hybridomas. However, monoclonal Fab fragments and IgG fragments can also be produced by other methods, for example by using bacteriophage to display and select polypeptide chains expressed from a V-gene library or genetic engineering.

Biologically functional antibody fragments are those fragments sufficient for binding to the desired stimulant drug, such as Fab, Fv, F(ab')$_2$, and sFv (single-chain antigen-binding protein) fragments. One can choose among these or whole antibodies for the properties appropriate to a particular method.

The chimeric antibodies can comprise proteins derived from two different species. The portions derived from two different species can be joined together chemically by conventional techniques or can be prepared as a single contiguous protein using genetic engineering techniques (See e.g. Cabilly et al., U.S. Pat. No. 4,816,567; Neuberger et al., WO 86/01533 and Winter, EP 0,239,400). Such engineered antibodies can be, for instance, a chimeric antibody comprising murine variable regions and human constant regions, or complementarity determining regions (CDR)-grafted antibodies (Tempest et al., Biotechnology 9:266–271, 1991). The constant region domains can be chosen to have an isotype most suitable for the intended application of the antibodies.

This invention encompasses a method of generating high affinity monoclonal antibodies and their antigen binding fragments (e.g., Fab) for use in treating the medical problems associated with stimulant drug abuse. d-Methamphetamine is the prototypic stimulant molecule because it has severe addiction liability and produces significant acute and chronic medical problems. Anti-methamphetamine monoclonal antibody (of any mammalian source) may be used as a prototypic, long acting stimulant antagonist for treating addiction. In contrast, smaller molecular weight fragments (like Fab) may be used as a prototypic shorter acting, less antigenic, more rapidly eliminated antagonist for treating drug overdose. Since intact antibody and smaller fragments like Fab are cleared by different organ systems, this approach will also provide a greater potential for altering and controlling the endogenous clearance and biological safety of these proteins.

In addition to the obvious benefits of a new therapeutic approach, there would be other important contributions. In as much as the binding properties of receptors and antibodies are similar in many ways, the careful design of amphetamine-like haptens could lead to the selection of antibodies that mimic aspects of the endogenous binding sites of these drugs in the CNS. Molecular studies of these antibody binding sites (through protein sequencing, structure-activity studies and molecular modeling) could aid in the prediction of the characteristics necessary for drug-receptor interaction at sites of action including neuronal transporters, vesicular storage systems, and with monoamine oxidase. Molecular studies of the sequence of the antibody binding site and the neuronal transporters may also yield important clues concerning the structural rules for molecular interactions of biologically active compounds. Furthermore, the use of these antibody models for screening peptide and organic combinatorial libraries could lead to discovery of novel agonists or antagonists for these neuronal transporters.

The present invention is directed to a monoclonal antibody that specifically recognizes a stimulant drug of abuse or a metabolite thereof. Representative drugs of abuse or such metabolites include d-methamphetamine, d-amphetamine, 3,4-methylenedioxymethamphetamine, and 3,4-methylenedioxyamphetamine and or structural-related analogs of these compounds. In one form, the antibody is of murine origin. Alternatively, the antibody is of human origin or contains portions of a human antibody.

The present invention is also directed to an antigen binding fragment that specifically recognizes a stimulant drug of abuse or a metabolite thereof. Representative drugs of abuse or metabolites are d-methamphetamine, d-amphetamine, 3,4-methylenedioxymeth-amphetamine, and 3,4-methylenedioxyamphetamine and or structural-related analogs of these compounds. In one form, the antibody is of murine origin. Alternatively, the antibody is of human origin or contains portions of a human antibody.

The present invention is also directed to a method of treating stimulant drug abuse, comprising the step of administering a pharmacological effective dose of the monoclonal antibody of the present invention to an individual in need of such treatment. Representative stimulant drugs are described above.

The present invention is also directed to a method of treating stimulant drug overdose, comprising the step of administering a pharmacological effective dose of the antigen binding fragment of the present invention to an individual in need of such treatment.

The present invention is also directed to a compound with the structure of

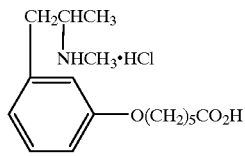

wherein said compound is (S)- or (R)-3-(5'-Carboxypentyloxy) methamphetamine hydrochloride.

The present invention is also directed to a method of generating a class-specific monoclonal antibody that recognizes methamphetamine-like stimulants, comprising the step of: immunizing animals with the compound of the present invention; generating antibody-secreting hybridomas from the spleen cells of said animals; and screening the specificity of the antibodies, wherein antibody showing cross-reactivity to methamphetamine-like stimulants indicates the generation of methamphetamine-like stimulants-specific antibody.

The present invention is also directed to a compound with the structure of

wherein R is a hydrocarbon chain with a carboxylic acid terminus, and R is attached to the aromatic ring at position selected from the group consists of 2, 3, and 4. This compound can possess ether (S)- or (R)-stereochemistry. In one embodiment, R is O(CH$_2$)$_X$COOH, and X is from 2 to 9. In another embodiment, R is OCH$_2$CH=CH(CH2)$_X$COOH, and X is from 1 to 6. In another embodiment, R is OCH$_2$C=C(CH2)$_X$COOH, and X is from 1 to 6. In another embodiment, R is O(CH$_2$)$_X$O(CH2)$_Y$COOH, and X is from 2 to 4, Y is from 1 to 5. In another embodiment, R is O(CH$_2$)$_X$NR1(CH2)$_Y$COOH, X is from 2 to 3, Y is from 1 to 5, and R1 is alkyl 1–5 carbon. In another embodiment, R is S(CH$_2$)$_X$COOH, and X is from 2 to 9. In another embodiment, R is SCH$_2$CH=CH(CH2)$_X$COOH, and X is from 1 to 6. In another embodiment, R is SCH$_2$C=C(CH2)$_X$COOH, and X is from 1 to 6. In another embodiment, R is S(CH$_2$)$_X$O(CH2)$_Y$COOH, and X is from 2 to 4, Y is from 1 to 5. In another embodiment, R is S(CH$_2$)$_X$NR1(CH2)$_Y$COOH, X is from 2 to 3, Y is from 1 to 5, and R1 is alkyl 1–5 carbon. In another embodiment, R is (CH$_2$)$_X$COOH, and X is from 3 to 8. In another embodiment, R is (CH2)$_X$CH=CHCOOH, and X is from 2 to 7. In another embodiment, R is (CH2)$_X$C=CCOOH, and X is from 2 to 7. In another embodiment, R is CH=CH(CH$_2$)$_X$COOH, and X is from 1 to 6. In another embodiment, R is C=C(CH2)$_X$COOH, and X is from 1 to 6.

In another embodiment, the present invention further comprises of a hydrocarbon structure R1 attached to R, wherein R1 is selected from the group consisting of —CH$_2$CH$_2$CN,

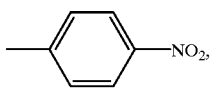 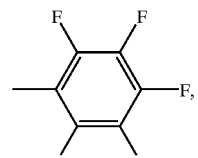

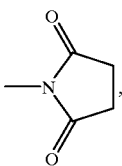 and 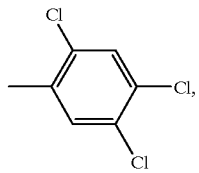

wherein said structure R1 couples said compound to a protein to form an immunogen for the generation of antibodies against methamphetamine-like stimulants.

The following examples are given for the purpose of illustrating various embodiments of the invention and are not meant to limit the present invention in any fashion.

EXAMPLE 1

Generation of High Affinity Monoclonal Antibodies and Fab Fragments that Bind to D-Methamphetamine and Other Stimulant Drugs The haptens are coupled to a bovine serum albumin antigen by using a general synthesis procedure (6). This two-step, modified carbodiimide procedure permits a defined number of haptens to be covalently bound to the protein in a controlled molecular orientation. It also minimizes the cross linking of protein molecules, and the unwanted conjugation of the haptens through the free amino group on the d-methamphetamine haptens. A complimentary ovalbumin-d-methamphetamine hapten for use in screening hybridoma products in an enzyme-linked immunosorbent assay (ELISA) and for use in testing for antibody production after active immunization of rats with a BSA-d-methamphetamine hapten was also generated. This general synthesis procedure has been used in the past to generate anti-drug antibodies (4) and anti-peptide antibodies (7).

For the production of monoclonal antibodies, BALB/c mice (n=6–10 per hapten) are immunized with 100 μg of the BSA-d-methamphetamine, emulsified in an equal volume of an adjuvant (e.g., Titer Max, RIBI, Freund's Complete Adjuvant). One month later the animals were boosted with the same reagents and two weeks later the serum was tested for specific antibodies using the ovalbumin-d-methamphetamine conjugates in an ELISA. The spleen from the animal with the highest titer of anti-d-methamphetamine antiserum was used for the first fusion. The other animals were boosted every three to four weeks to maintain titers of anti-d-methamphetamine in anticipation of future immunizations. After fusion of spleen cells from the mice with a myeloma cell line, hybridomas secreting anti-d-methamphetamine antibodies were identified using an ELISA with the appropriate ovalbumin-d-methamphetamine conjugate as described (7).

Wells with a positive reaction to d-methamphetamine were subcloned to monoclonality. For specificity determinations, the antibodies were tested in an ELISA format using a series of ligands. These ligands include (but are not limited to) d- and l-methamphetamine, d- and l-amphetamine, MDMA, MDA, ephedrine, pseudoephedrine, and other potentially cross reacting stimulant-like molecules and endogenous neurotransmitters. Antibodies specific for the d-isomers and having a low Kd value (e.g., <1–30 nM) were selected. Although a range of antibody affinities has been studied (as great as 250 nM), the objective was to have affinity constants for methamphetamine in the range of 1–30 nM.

Once an anti-d-methamphetamine secreting hybridoma was chosen, large quantities of the antibody were produced in a hollow fiber bioreactor (3). A representative method for the monoclonal antibody purification process is as follows. After production, the monoclonal antibody-containing tissue culture media was combined and concentrated to one-tenth of the original volume using an Amicon spiral cartridge concentration system. This technique takes approximately 10 minutes to concentrate 2 L down to 100–200 ml. The procedure recovers 95% of the monoclonal antibody and removes >95% of the bovine albumin in the media. The concentrated monoclonal antibody was dialyzed against 50 mM MES buffer (2-(N-Morpholino)-ethanesulfonic acid), pH 6.0 for further purification using a large, glass chromatography column packed with 1L of SP-Sepharose Big Bead media (Pharmacia LKB Biotechnology). The sample was loaded on the column and washed with the MES buffer to remove non-specifically bound proteins. The monoclonal antibody was eluted in one step using 50 mM MES/0.15 M NaCl. This elution also serves to reconcentrate the monoclonal antibody. The purity and concentration of the purified anti-d-methamphetamine monoclonal antibody were determined by SDS-PAGE (5) and spectrophotometry respectively.

The Fab fragments of the monoclonal antibody were produced by the papain digestion method described by Goding (8) using an MAb:papain ratio of 500:1 (w/w). After digestion, the Fab was purified using a HPLC column containing Pharmacia Streamline DEAE Sepharose anion exchange media. Purity was checked by SDS-PAGE and the protein concentration measured with a Coomassie protein assay or spectrophotometrically. For every 100 g of monoclonal antibody, one may expect to yield at least 55–68 g of Fab fragments. For use in animals, the Fab and monoclonal antibody were dialyzed against PBS, pH 7.4 and concentrated with an Amicon ultrafiltration device to 50–100 mg/ml (depending on the needs of the in vivo testing procedure). Both Fab and monoclonal antibody were stored at −80° C. until needed. There was no decrease in binding activity or solubility after long-term storage of the monoclonal antibody or Fab.

EXAMPLE 2

Synthesis of Hapten

Figure 3:
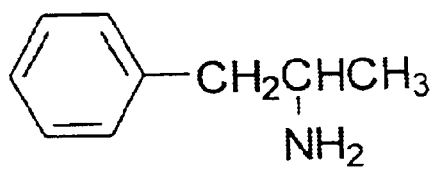
FIG. 3 shows the structures of methamphetamine-like stimulants.
Figure 3:
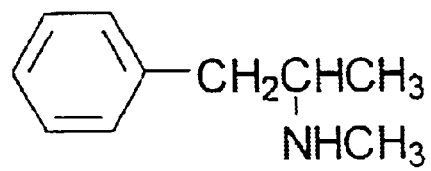
Figure 3:
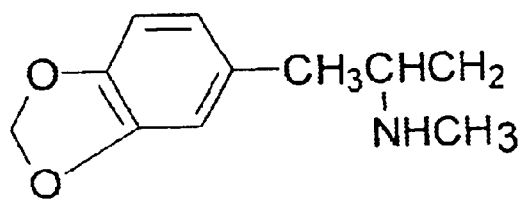
Figure 4A:
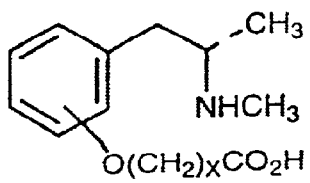
FIGS. 4A–4C show the hapten 1 to hapten 15 designed for generating antibodies that are specific for methamphetamine-like stimulants.
Figure 4A:
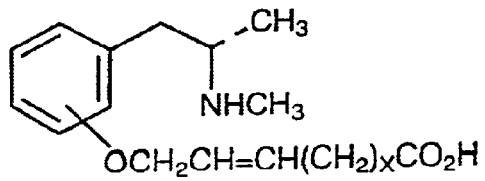
Figure 4A:
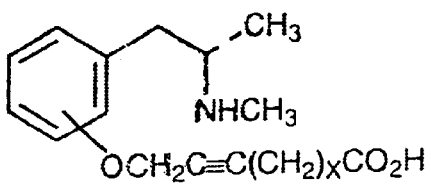
Figure 4A:
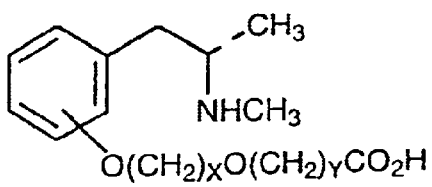
Figure 4A:
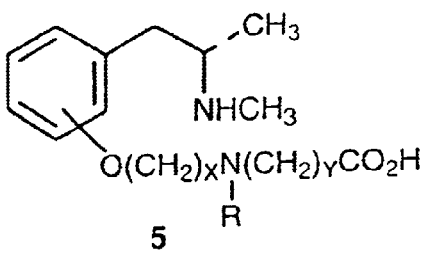
Figure 4B:
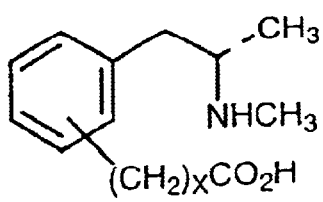
Figure 4B:
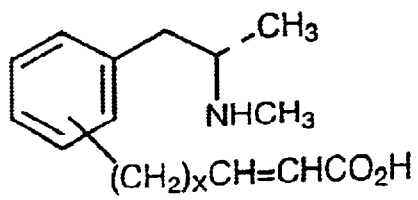
Figure 4B:
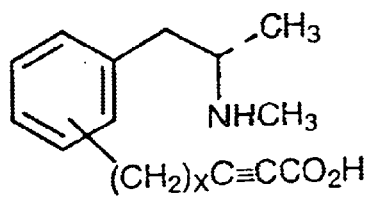
Figure 4B:
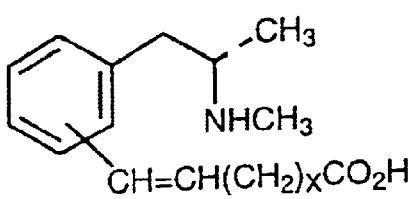
Figure 4B:
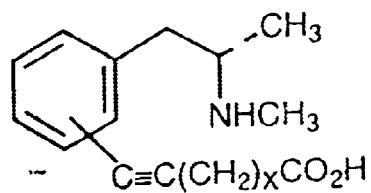
Figure 4C:
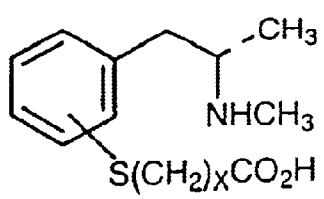
Figure 4C:
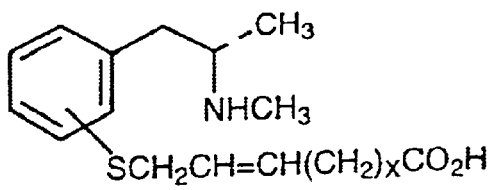
Figure 4C:
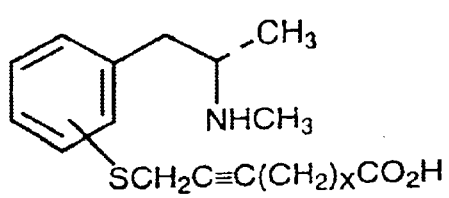
Figure 4C:
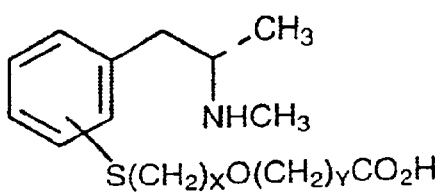
Figure 4C:
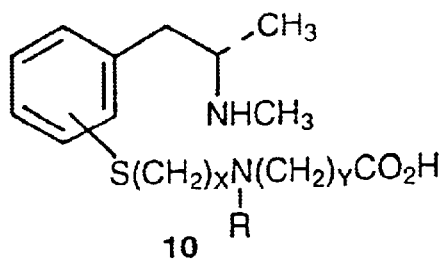

One goal of the present invention was to generate a class-specific monoclonal antibody that could be used as a pharmacokinetic antagonist for treating the medical problems associated with methamphetamine-like stimulants. The methamphetamine-like stimulants that are most often abused are methamphetamine, amphetamine and MDMA (see FIG. 3). Based on review of the literature on anti-methamphetamine antibodies (e.g., Faraj et al., 1976; Usagawa et al., 1989; Ward et al., 1994) and analysis of the molecular features of the molecules shown in FIG. 3, it is hypothesized that coupling of a spacer group (with a carboxylic acid terminus) at the para or meta position of the aromatic ring structure will offer the best chance for generating a class-specific antibody. The resulting antibodies are expected to react best with the parent compound, as opposed to metabolites, and would also be less likely to significantly cross react with natural neurotransmitters. If the protein was coupled to the amine groups at the other end of the molecule (which would be more convenient), this would not generate antibodies that would cross react with MDMA. The haptens designed for generating antibodies specific for methamphetamine-like stimulants are illustrated in FIGS. 4A–4C.

Figure 5:
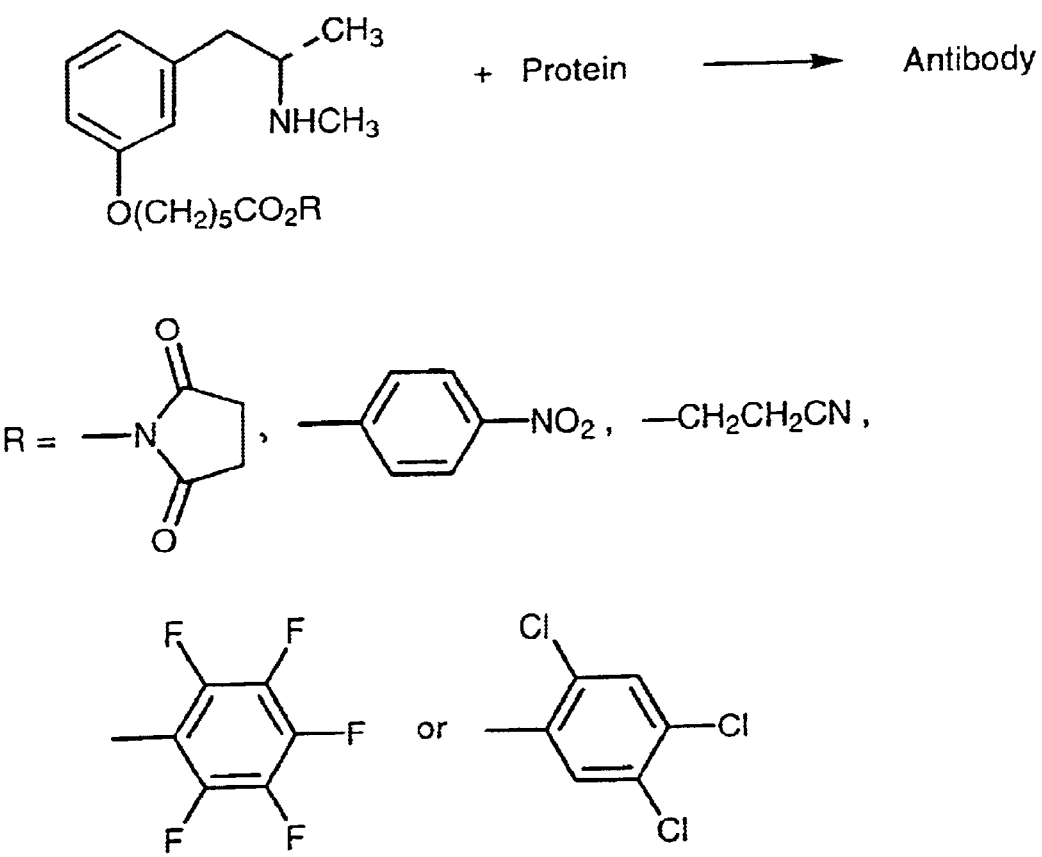
FIG. 5 shows a method of using activated ester to couple the hapten to a protein to make the antibody. Similar chemistry would apply to all other structures shown in FIGS. 4A–4C.

A method of using activated ester to couple the hapten to a protein to make the antibody is shown in FIG. 5. Similar chemistry would apply to all other structures shown in FIGS. 4A–4C.

Figure 6:
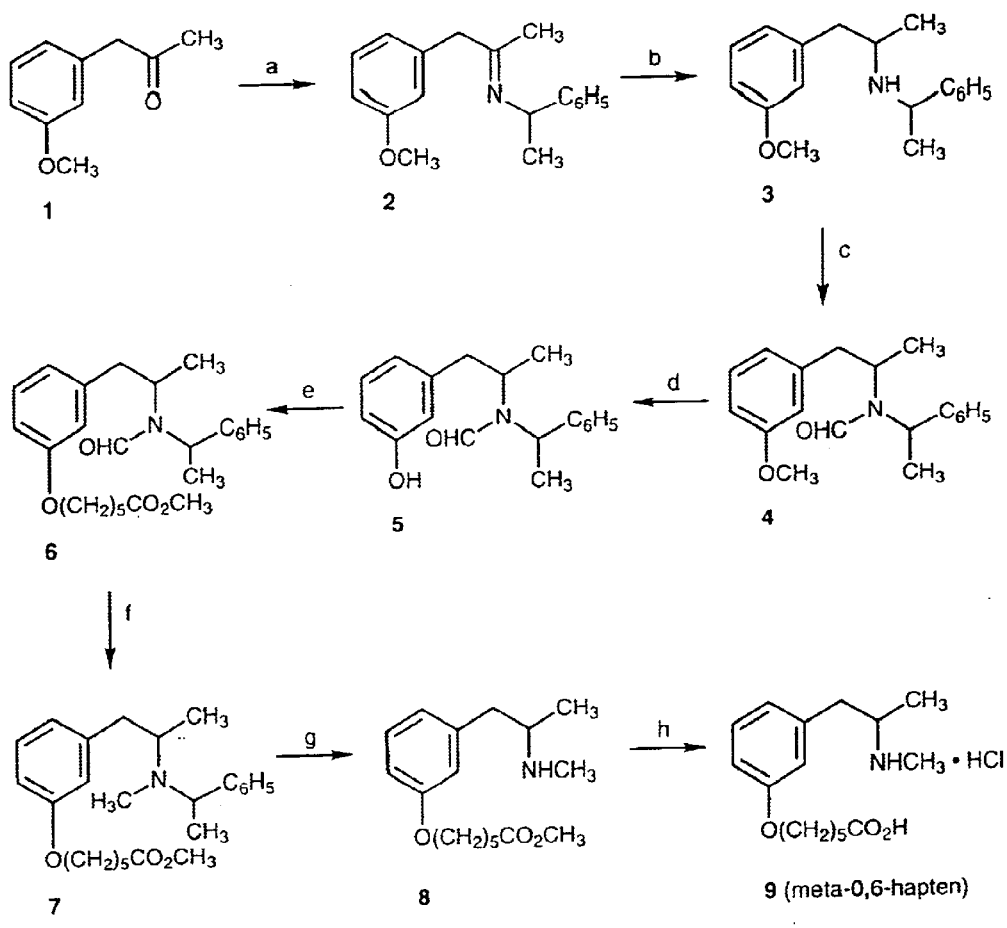
FIG. 6 shows the scheme of synthesis for 3-(5'-carboxypentyloxy)methamphetamine hydrochloride.

The synthesis of one of the haptens (hapten 1 in FIG. 4A with X=5 and connected at the 3-position) is outlined in FIG. 6. The goal is to prepare the (S)-(+)-isomer of 3-(5'-carboxypentyloxy)methamphetamine (9). To establish the feasibility of the synthetic methods, the synthesis of (R)-(−)-9 is presented. Those skilled in the art will know that (S)-(+)-9 can be prepared using exactly the same method starting with (S)-α-methylbenzylamine.

Thus, to prepare (R)-9, 3-methoxyphenylacetone (1) was condensed with (R)-α-methylbenzylamine to give 2. Raney nickel reduction of 2 followed by separation provided the pure (R,R)-diastereoisomer 3. The N-formyl-protected intermediate 4 was obtained by treating 3 with a formic acid-acetic anhydride mixture. O-Demethylation of 4 using boron tribromide yielded the phenol 5. Alkylation of 5 with methyl 6-bromohexanoate afforded 6. Reduction of 6 using diborane provided the N-CH$_3$ intermediate 7, which yielded 8 on reduction using palladium on carbon catalyst in refluxing formic acid. The desired final optically pure hapten 9 as the hydrochloride salt was obtained by treating 8 with dilute hydrochloric acid.

EXAMPLE 3

Synthesis of (R,R)-N-α-methylbenzyl-3-methoxyamphetamine (3) hydrochloride

A solution of 3-methoxyphenylacetone (10 g, 0.061 mol) and (R)-α-methylbenzylamine (7.38 g, 0.061 mol) in 100 mL of dry toluene was heated to reflux in a flask fitted with a Dean-Stark condenser for 20 h. After cooling the reaction mixture, the solvent was removed, and the residue was dried under vacuum. The residual oil was dissolved in absolute EtOH (60 mL), and a slurry of EtOH washed Raney nickel was added. The resulting mixture was hydrogenated for 96 h at 40 psi hydrogen. The catalyst was removed by filtration over a Celite bed, and the filtrate was treated with HCl gas. Evaporation of the solvent gave a white solid which was triturated with hot acetone to provide the target compound 3 as a white solid. An analytical sample was prepared from an aliquot removed. The sample recrystallized from MeOH/diethyl ether had mp 215–218° C.; $[\alpha]^{21}D$ (17.85°, c 1.95, MeOH). $^1$H NMR (CD$_3$OD) δ 1.17 (d, 3H), 1.69 (d, 3H), 2.53 (dd, 1H), 3.17 (m, 1H), 3.31 (m, 1H), 3.74 (s, 3H), 4.63 (q, 1H), 6.59 (s, 1H), 6.62 (d, 1H), 6.82 (d, 1H), 7.21 (t, 1H), 7.54 (m, 5H). Elemental analysis: calcd. for C$_{18}$H$_{23}$NO.HCl: C, 70.69; H, 7.91; N, 4.58; Cl, 11.59. Found: C, 70.51; H, 7.99; N, 4.53; Cl, 11.65.

EXAMPLE 4

Synthesis of (R,R)-N-formyl-N-α-methylbenzyl-3-methoxyamphetamine (4)

To a stirred solution of formic acid (7.5 mL, 0.2 mol) at 0° C. was added acetic anhydride (18.9 mL, 0.2 mol) dropwise. After 30 min, the amine 3 (3.9 g, 13.7 mmol) in a minimum volume of formic acid was added, and the mixture was stirred overnight. Water was carefully added, and the mixture was neutralized with dilute $NH_4OH$. The mixture was extracted with $CH_2Cl_2$, washed with saturated sodium chloride solution, and dried over $NaSO_4$. The residue obtained after evaporation was purified on a silica gel column eluting with a solvent mixture of hexane/$CH_2Cl_2$/$CH_3OH$ (5:14:1) to give 3.83 g (94%) of 4 as a white solid.

EXAMPLE 5

Synthesis of (R,R)-N-formyl-N-α-methylbenzyl-3-hydroxyamphetamine (5)

To a stirred solution of 4 (2.85 g, 10 mmol) in $CH_2Cl_2$ (30 mL) was added a solution of $BBr_3$ (4.84 g, 20 mmol) in 50 mL of $CH_2Cl_2$. After stirring overnight, the excess of $BBr_3$ was quenched by careful addition of water and the organic fraction separated. The aqueous layer was further extracted with $CH_2Cl_2$, and the combined $CH_2Cl_2$ fraction was dried over $Na_2SO_4$. Evaporation gave 2.01 g (74%) of 4 as a white solid. Further purification on a silica gel column eluting with hexane/$CH_2Cl_2$/MeOH (4:8:1) gave 1.65 g (61%) pure product. The analytical sample was triturated with ether to give white crystals; mp 174–177° C. Elemental analysis: calcd. for $C_{18}H_{21}NO_2.1.25 H_2O$: C, 75.69; H, 7.50; N, 4.91. Found: C, 75.67; H, 7.46; N, 5.00.

EXAMPLE 6

Synthesis of (R)-3-(5'-carbomethoxypentyloxy) Methamphetamine (8) hydrochloride

To a suspension of hexane washed sodium hydride (216 mg, 4.32 mmol) in 5 mL of DMF was added a solution of (R,R)-3-hydroxyphenyl-2-propyl-N-formamido-N-α-methylbenzylamine (5) (1.22 g, 4.32 mmol). After stirring for 30 min at room temperature, a solution of methyl 6-bromohexanoate (1.36 g, 6.48 mmol) in DMF (3 mL) was added and stirred overnight at room temperature. The reaction mixture was diluted with $H_2O$ (50 mL) and extracted with methylene chloride (3×10 mL). The combined organic fraction was washed with saturated sodium chloride solution and dried over $Na_2SO_4$. After removal of the solvent, the residue was purified on a silica gel column. Eluting with a solvent mixture ($CH_2Cl_2$:hexane:MeOH, 4:14:1) to give 1.68 g (95%) of 6. $^1H$ NMR (($CDCl_3$) δ 1.28 (dd, 3H), 1.53 (m, 2H), 1.58 (dd, 3H), 1.72 (m, 4H), 2.36 (m, 2H), 2.41 (m, 1H), 2.89 (m, 1H), 3.25 (m, 1H), 3.41 (t, 2H), 3.68 (s, 3H), 3.82 (q, 2H), 4.58, 6.07 (2 q, 1H), 6.17, 6.67 (2 s, 1H), 6.57, 6.40 (2d, 1H), 6.67 (dd, 1H), 7.05 (dd, 1H), 7.36 (m, 5H), 8.41, and 8.48 (two s, 1H). The sample was used in the next step without further characterization.

A solution of the above formamide (1.63 g) was treated with $BH_3.THF$ (10 mL) and stirred for 30 min when the excess of $BH_3$ was decomposed with MeOH followed by dilute HCl. The reaction mixture was basified with dilute $NH_4OH$ and extracted with methylene chloride (3×25 mL). The organic fraction was dried over $Na_2SO_4$ and evaporated to dryness. The oily material was dissolved in MeOH (25 mL), and Pd/C (250 mg) was added. The mixture was heated to reflux with formic acid (3 mL in three portions) for an hour. The filtrate, obtained after removal of the catalyst, was evaporated and the resulting residue purified on a silica gel column. Elution with 10% MeOH in methylene chloride gave 0.84 g (70% overall in two steps) of a clear oil. $^1H$ NMR (($CDCl_3$) 1.06 (d, 3H), 1.50 (m, 2H), 1.71 (m, 2H), 1.80 (m, 2H), 2.33 (t, 2H), 2.41 (s, 3H), 3.67 (s, 3H), 3.95 (t, 2H), 6.75 (m, 3H), 7.19 (m, 1H). The sample was converted to HCl salt; mp 53–57° C. Elemental analysis: calcd. for $C_{17}H_{27}NO_3.HCl.0.75 H_2O$: C, 59.50; H, 8.50; N, 4.10. Found: C, 59.65; H, 8.45; N, 4.21.

EXAMPLE 7

Synthesis of (R)-3-(5'-carboxypentyloxy) methamphetamine (9) hydrochloride

A solution 8 (400 mg, 1.15 mmol) in dilute hydrochloric acid (6N, 5 mL) was heated to reflux for 4 h. The reaction was evaporated to dryness, and the residue was crystallized from MeOH/ether to give 215 mg (59%) of an off-white crystalline material: mp 73–77° C. $^1H$ NMR ($CD_3OD$) 1.25 (d, 3H), 1.34 (m, 2H), 1.40 (m, 2H), 1.67 (m, 2H), 2.65 (t, 2H), 2.72 (s, 3H), 4.22 (m, 2H), 6.73 (m, 3), 7.13 (s, 1H). Elemental Analysis: calcd. for $C_{16}H_{25}NO_3.HCl.0.25 H_2O$: C, 59.99; H, 8.34; N, 4.37; Cl, 11.07. Found: C, 60.09; H, 8.33; N, 4.37; Cl, 11.13.

EXAMPLE 8

Effect of Hapten Design on Antibody Specificity for D-Amphetamine Like Drugs

In these experiments, rabbit antiserum was generated against two unique d-methamphetamine like haptens. Each hapten included the basic chemical structure of d-methamphetamine, along with a new chemical linker group attached at the para (para-O,6 hapten) or meta (meta-O,6 hapten) positions of the aromatic ring structure. The distal end of this linker group had a carboxy terminus for use in forming a peptide bond with protein antigens. After synthesis of a hapten-bovine serum albumin conjugate, this antigen was used for immunizing two rabbits. The first immunization for each rabbit was with 200 μg of either para-O,6 antigen or meta-O,6 antigen in Freund's complete adjuvant. The first booster immunization was with 100 μg of antigen in Freund's incomplete adjuvant. Seven to ten days later each animal was bled and the serum was collected for testing.

After titering each antiserum for selection of an appropriate serum dilution for radioimmunoassay, the relative cross-reactivity of each antiserum was determined. In this assay, a constant dilution of antiserum and a constant amount of [$^3H$]-methamphetamine was added to each test tube. Next, increasing amounts of either d-amphetamine or d-methamphetamine were added to separate tubes. After an overnight incubation at 4–8° C., the antibody bound [$^3H$]-methamphetamine was separated from the free [$^3H$]-methamphetamine using a goat anti-rabbit second antibody. The antibody precipitate in each tube was then transferred to a scintillation vial and the amount of radioactivity in each tube was determined by liquid scintillation spectrometry. For each of the test drugs (either d-amphetamine or d-methamphetamine), the $ED_{50}$ value for inhibition of [$^3H$]-methamphetamine binding to each antiserum was determined using a sigmoidal (logistic) fit to the percentage of [$^3H$]-methamphetamine binding versus log ligand dose.

Figure 7:
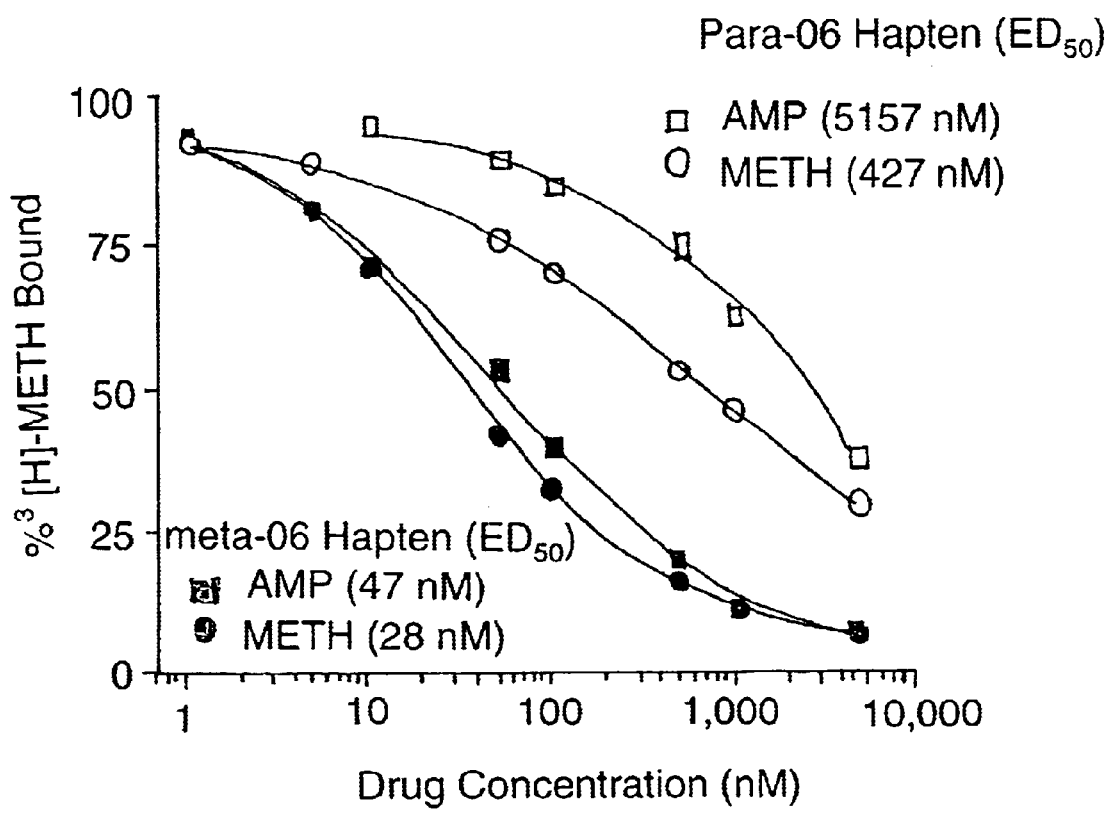
FIG. 7 shows radioimmunoassay cross-reactivity studies. The right two dose response curves show antiserum generated from immunization of two different rabbits with a para-O,6 d-methamphetamine hapten (hapten 1 in FIG. 4A with X=5 and connected at the 4 position). The left two dose response curves show antiserum generated from immunization with a meta-O,6 d-methamphetamine hapten (hapten 1 in FIG. 4A with X=5 and connected at the 3 position). The inhibition of [$^3$H]-methamphetamine binding for both antiserum was tested using both d-amphetamine and d-methamphetamine. These data shows that careful hapten design can leads to antiserum that has significant cross-reactivity with both d-amphetamine and d-methamphetamine.

Results from these studies show that the antiserum generated from the para-O,6 hapten (right two dose-response curves, FIG. 7) is significantly more specific for d-methamphetamine ($ED_{50}$=427 nM) than it is for d-amphetamine ($ED_{50}$=5157 nM). Indeed the relative cross reactivity for d-amphetamine is only 8.3% (427 nM/5157 nM×100%) of the value for d-methamphetamine. Thus, while this hapten might be useful in developing a highly specific assay for detection of d-methamphetamine, it would not be useful in generating a monoclonal antibody-based medication with high affinity and broad recognition for d-amphetamine like drugs.

In contrast, results from the radioimmunoassay analysis of the meta-O,6 antiserum (left two dose-response curves, FIG. 7) showed d-amphetamine ($ED_{50}$=47 nM) cross-reactivity is 59.6% (28 nM/47 nM×100%) of the value for d-methamphetamine ($ED_{50}$=28 nM). In these studies the meta-O,6 hapten also generated higher affinity antiserum than the para-O,6 hapten, as determined from the significantly lower $ED_{50}$ values for both d-amphetamine and d-methamphetamine. As an object of this invention is to generate a widely cross-reacting antiserum for d-amphetamine-like drugs, these data show the importance and uniqueness of the hapten design.

EXAMPLE 9

Comparison of Active and Passive Immunization as Treatments for D-Methamphetamine Addiction A series of male Sprague-Dawley rats were immunized with a d-methamphetamine-like hapten until high titers were achieved, or treated with anti-d-methamphetamine MAb. The rats were then repeatedly challenged with i.v. d-methamphetamine over several weeks. The ability of the antibodies to antagonize drug effects over an extended time period was assessed using d-methamphetamine dose-response curves with dosing schedules that are designed to simulate repeated binge use of the drug, and behavioral measurements of response. The rats for all of these studies were purchased with indwelling jugular venous catheters for i.v. administration of d-methamphetamine and anti-d-methamphetamine MAb.

For active immunization, one group of rats (n=6 for all groups) was immunized over a six week period prior to the start of the studies. An example immunization plan was 100 μg of the BSA-d-methamphetamine, emulsified in an equal volume of Titer-Max as the adjuvant, followed at weeks 3 and 6 by a booster immunization. Ten days after the last boost, the anti-d-methamphetamine serum titers are checked in an ELISA. If the titers are elevated, behavioral testing begins on day 10–14 after the last boost. For passive immunization, another group of rats was treated with 400 mg dose of monoclonal antibody the day before the start of the study. This dose of anti-d-methamphetamine monoclonal antibody (400 mg) should have the capacity to bind up to 2.1 mg/kg of d-methamphetamine on day 1 of the behavioral experiments, and up to 0.52 mg/kg of d-methamphetamine on day 16 (our final day of testing, see below). A 2.1 mg/kg dose of d-methamphetamine in the rat would be about equivalent to a 150 mg binge use of d-methamphetamine in an average size human (i.e., about 150 lbs). The calculation of the d-methamphetamine (M.W. 149 g/mol) mol-eq dose of IgG assumes a 350 g rat, two IgG binding sites, a mass of 150,000 kDa, an in vivo first-order monoexponential loss of the IgG, and an IgG t1/2 of 8.1 days (9).

The effectiveness of each therapy was measured by accessing the cumulative behavioral effects after administration of a range of d-methamphetamine doses over a 3 hr time period. This d-methamphetamine dosing strategy was used to simulate binge drug use, and an addict's attempt to surmount the blocking effects of the antagonist by the self-administration of progressively higher doses. The i.v. doses of 0.1, 0.3 and 1.0 mg/kg are administered at 0, 1.5 hrs and 3.0 hrs, respectively. This simulated binge dosing was repeated every 4 days (day 1, 4, 8, 12 and 16) for up to 16 days.

The EthoVision system, which has video tracking and digitized motion analysis, was used for continuous behavioral monitoring. d-methamphetamine-induced locomotor activity, e.g., distance traveled, percentage of the time spent moving, and animal rearing, were measured over a 6 hr period. From each day of behavioral experiments, the time to maximum effects after each dose of d-methamphetamine, the maximum effect, the area under the behavioral effect curve from the time of dosing to the end of each type of behavioral effect, and the duration of effects were calculated. The end of each behavioral effect was based on a statistical analysis of the average baseline response prior to drug administration. For instance, the point at which the animals' response has returned to 1+S.D. of the mean pre-drug response for two consecutive 2 min intervals. The data were analyzed by a two-way (dose of d-methamphetamine and time) repeated measures ANOVA, followed by a Student-Newman-Keuls post hoc test. The results were considered significant at $P<0.05$.

EXAMPLE 10

Effect of Anti-D-Methamphetamine Mab on Pharmacokinetics and Behavior After Stimulant-Induced Toxicity in Rats The ability of immunotherapy to reverse toxicity resulting from high doses of d-methamphetamine was examined as follows. For the pharmacokinetic studies, antibody-induced changes in d-methamphetamine disposition, protein binding, and the tissue distribution of d-methamphetamine in rats are examined. For behavioral studies, changes in d-methamphetamine-induced behavioral effects, the time needed for the reversal of effects, and pharmacokinetic and pharmacodynamic relationships are examined.

To characterize the plasma concentration-time profiles of d-methamphetamine, anti-d-methamphetamine monoclonal antibody and anti-d-methamphetamine Fab following i.v. administration, male Sprague-Dawley rats (n=4 per group) purchased with indwelling jugular venous and femoral arterial catheters are placed in a metabolic cage and injected with either d-methamphetamine (0.5 mg/kg of d-methamphetamine along with a tracer dose of [$^3$H]d-methamphetamine) or the appropriate antibody (100 mg of monoclonal antibody or 100 mg of Fab). The dose is administered as a 15 sec bolus dose via the jugular catheter. Aliquots of arterial blood are removed from the arterial catheter. The rats are kept in a metabolic cage for collection of urine, with free access to food and water. For each molecule (d-methamphetamine, MAb, Fab), the values for the volume of distribution at steady-state, systemic clearance, renal clearance, terminal elimination half-life, and the fraction of the drug appearing in the urine were calculated by using WinNonlin (Pharsight Corporation, Mountain View, Calif.). The equations for these calculations can be found in the text by Gibaldi and Perrier (10).

The effect of the anti-d-methamphetamine Fab on the tissue distribution of d-methamphetamine was determined in the following representative method of analysis. Rats were injected with d-methamphetamine (0.5 mg/kg along with a tracer dose of [$^3$H]d-methamphetamine) as a 15 sec i.v. bolus via their jugular catheter. At 30 min after d-methamphetamine administration, Fab-treated animals (n=3 per time point×10 tissue collection time points from 45 min to 24 hrs) received an i.v. injection of monoclonal anti-d-methamphetamine Fab in 1 ml of phosphate-buffered saline (pH 7.4). The dose of anti-d-methamphetamine Fab administered to each animal was approximately mol-eq in binding sites to the amount of d-methamphetamine remaining in the rat at 30 min (or about 80% of the i.v. d-methamphetamine dose). At 30, 45, 60, 90 120, 210, 300 min and 8, 18 and 24 hrs after drug administration, the animals were anesthetized with diethyl ether (in a laboratory hood for safety) and blood was collected from the posterior vena cava. Blood, brain, liver, heart, lung, right kidney, and right testis were harvested as quickly as possible in this order. The tissues were rinsed with water, weighed, and quick frozen in liquid nitrogen. Blood samples were allowed to clot and then centrifuged for plasma collection. Plasma and organ samples were stored at −80° C. until extracted and analyzed for d-methamphetamine using a HPLC method similar to that published by Burchfield et al. (11). Briefly, plasma samples were alkalinized with sodium carbonate and extracted with hexane. After mixing and centrifugation, the hexane phase were acidified with 0.1N HCl, mixed, and centrifuged. The HCl phase was injected into the HPLC column. The mobile phase consists of 1% phosphoric acid, 4 mmol/L dodecyl sodium sulfate with 20% acetonitrile at 2 ml/min, using a reverse phase column. Tissue samples were weighed and homogenized with HCl and the propylamphetamine internal standard. This homogenate mixture was processed exactly as the plasma samples for d-methamphetamine determination.

For determining the ability of antibodies to reverse acute toxicity, dose of d-methamphetamine that produces significant toxic effects, but not a life threatening dose, was administrated. The dose was selected based on d-methamphetamine dose-behavioral response studies conducted in the laboratory. In the treatment experiments, the anti-d-methamphetamine Fab was injected at least 30 min after the d-methamphetamine when effects are maximal. The doses of anti-d-methamphetamine Fab were administered in equimolar amounts to the amount of methamphetamine remaining in the animal at 30 minutes. For control treatments, the animals were administered saline or an anti-phencyclidine (anti-PCP) monoclonal antibody (of the same isotype). This anti-PCP monoclonal antibody provides a negative antibody control since this antibody does not cross-react with d-amphetamine-like drugs. The animals are allowed to recover for at least 3 days between treatments (saline, anti-PCP monoclonal antibody, anti-Meth Fab in a repeated-measures, mixed-sequence design). The success of the therapy is determined by statistically significant changes in behavioral measures. The behavioral data from total movement, distance traveled, rearing and the duration of each behavioral effect are normalized to a percentage of the maximal response of the drug for each animal without antibody treatment.

EXAMPLE 11

Use of Monoclonal Antibodies to Treat a Methamphetamine-Induced Drug Overdose in Male Rats (a Preclinical Model of Human Drug Overdose)

The hapten used for the production of the monoclonal antibodies was similar in design to the para-4 hapten described in Example 3. This hapten design is known to generate highly selective antibodies for d-methamphetamine, which do not have significant cross-reactivity with d-amphetamine. Thus, in this rat model of human overdose the antibody will bind to d-methamphetamine, but it is not expected to completely reduce METH-induced toxicity since pharmacokinetic studies of intravenous d-methamphetamine in the rat show there is significant amount of the psychoactive d-amphetamine metabolite in the brain. Nevertheless, these studies provide the proof of concept that monoclonal anti-methamphetamine monoclonal antibody fragments can produce beneficial therapeutic effects resulting for a d-methamphetamine overdose.

EXAMPLE 12

Production of Antibodies

Monoclonal antibodies were produced against a methamphetamine-like hapten with a four-member spacer group attached at the para position of the aromatic ring structure of methamphetamine (hapten 11 in FIG. 4C with X=3 and connected at the 4 position). The hapten was covalently bound to bovine serum albumin, through a covalent peptide bond at the end of the four-carbon spacer group away from its attachment to the aromatic ring structure of methamphetamine. The anti-methamphetamine monoclonal antibodies were produced from cell line 6H8 in a Cell-Pharm System hollow bioreactor (Unisyn Technologies, Inc., Hopkinton, Mass.), as described elsewhere (Valentine et al., 1996). Monoclonal IgG from the bioreactor product was purified using a two-step procedure. Cell culture media was diluted (1:5) with deionized water and the pH adjusted to 6.0 with HCl. This solution was passed through a cation exchange SP Sepharose Big Beads (Pharmacia Biotech) chromatography column. The column was rinsed with buffer (MES Buffer 50 mM pH 6.0). When the absorbance returned to baseline IgG was eluted using buffer (MES 50 mM pH 6.0 containing 150 mM NaCl).

The Fab fragments were prepared from the purified monoclonal IgG by the method described by McClurkan et al. (1993) for the purification of anti-PCP Fab fragments. Purified anti-methamphetamine Fab fragments were then concentrated and the buffer changed to sodium phosphate 15 mM pH 7.2 containing 150 mM of NaCl, using a high pressure concentrator system (Amicon, Beverly, Mass.). The final concentration of Fab was between 40 and 50 mg/ml. The quality and purity of product were checked using SDS-Page, immunoelectrophoresis, isoelectric focusing and by running it through a molecular size column. According to SDS-Page and molecular weight sizing column, the anti-methamphetamine Fab preparation was at least 95% pure. The monoclonal anti-PCP Fab, which was used as a control antibody, was prepared in the same manner.

EXAMPLE 13

Behavioral Testing of the Anti-Meth Antibody Medication

Adult male Sprague-Dawley rats (300 g) were purchased from Hilltop laboratories (Scottsdale, Pa.), with a cannula implanted in the right jugular vein. These cannulae were used for all injection of saline, drug and treatments (saline, anti-PCP Fab and anti-METH Fab). Prior to the beginning of the experiments, rats were allowed to habituate to the behavioral testing environment (an 1.5×3 ft open top polypropylene chamber containing gray non-reflective gravel). Behavioral analysis was conducted by the methods of Hardin et al. (1998). This method allowed the accurate quantitation and comparison of the distance traveled and the number of rearing events during the entire testing period. These behavioral measurements were used as sensitive indicators because of the potent effect that d-methamphetamine has on rodent spontaneous locomotor activity.

All dosing for behavioral measurements was conducted in a repeated-measures, mixed-sequences protocol. Rats were placed in the chambers 60 minutes before the administration of any saline, drug or treatments. Saline or d-methamphetamine was administered at time 0 for all groups, as a no effect control (saline) or to produce drug effects (d-methamphetamine). Saline or anti-methamphetamine Fab or anti-PCP Fab (in a 3 ml final volume) was administered at time 30 minutes, to determine the effects of no treatment (saline) or a control monoclonal antibody (a monoclonal anti-PCP Fab or a control monoclonal antibody that does not bind methamphetamine) or the test treatment (monoclonal anti-methamphetamine Fab from hybridoma cell line 6H8).

Each rat received four different treatments. The treatments were: saline followed by saline (for determination of baseline activity), methamphetamine followed by saline (for determination of baseline methamphetamine-induced effects), methamphetamine followed by anti-PCP Fab (for determination of the baseline effect of a matched antibody control that does not bind to methamphetamine), and methamphetamine followed by anti-methamphetamine Fab (to determine if the methamphetamine-specific therapy has any effects on the methamphetamine-induced overdose). The dose of Fab (either anti-PCP or anti-methamphetamine Fab) was calculated to have sufficient capacity to neutralize the body burden of methamphetamine at the time of administration (i.e., 30 min after the methamphetamine administration). The amount administered was a mole-equivalent dose of Fab to the methamphetamine in the rat at 30 min after the intravenous injection of methamphetamine. These calculations were based on the methamphetamine pharmacokinetic parameters determined by Reverie et al., (1999).

Results from the administration of saline or methamphetamine without treatments were computer analyzed by summing the rat activity during 2-min measurement intervals from the time of injection of saline or methamphetamine (at time 0) until the end of the experiment. Results for each rat were normalized against the their baseline methamphetamine activity, resulting from the 1 mg/kg dose of methamphetamine (i.e., this treatment was considered 100% activity).

Results from experiments testing the effects of treatments (e.g., anti-methamphetamine Fab) were determined from the duration of action of the drug using a statistical approach. The mean +1 SD of the baseline activity (after saline injection, followed by a saline treatment at 30 minutes) was calculated from 36 minutes until the end of the experiment. For each experiment, METH effects were considered over when two consecutive 2-min testing intervals were equal to or below the mean +1 SD of the baseline rat activity. This analysis was conducted for both the measurements of distance traveled and the number of rearing events.

All values are expressed as mean±SD. Statistical comparisons of behavior experiments were determined using a one-way repeated-measure ANOVA. When the F value was significant ($P<0.05$), a post-hoc pairwise multiple comparison was conducted using a Student-Newman-Keuls test. The level of significance was set at $P<0.05$.

EXAMPLE 14

Effects of Anti-Meth Fab on Meth-Induced Behavioral Effects

Figure 8A:
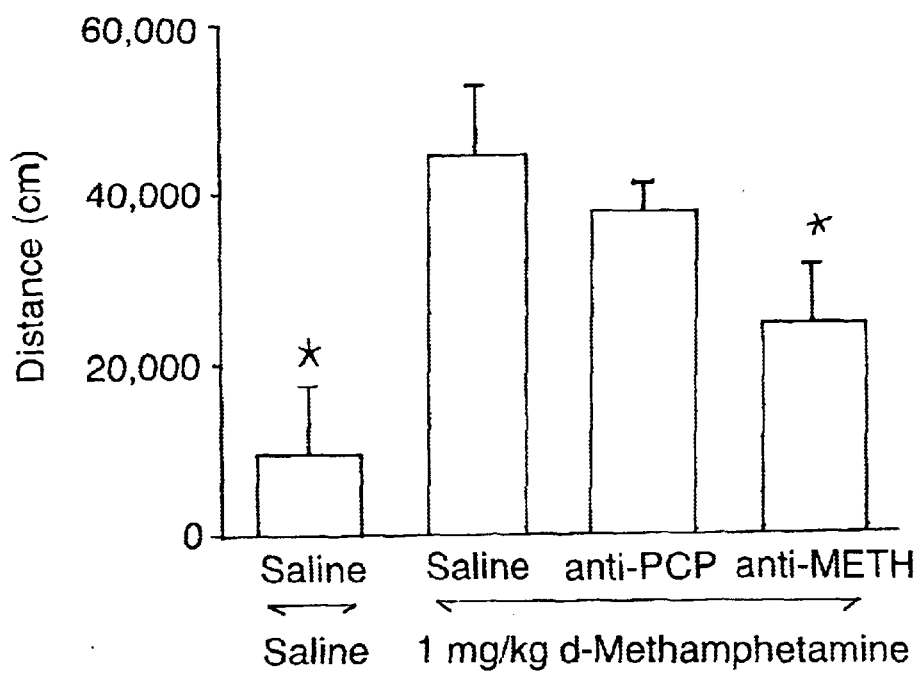
FIG. 8A shows the distance travel from 30 minutes after saline or d-methamphetamine administration until the end of the experiment, 4.5 hours later. *$p<0.05$ compared to a 1 mg/kg dose of methamphetamine followed by the saline control treatment. †$p<0.05$ compared to a 1 mg/kg dose of methamphetamine followed by the anti-methamphetamine Fab treatment.
Figure 8B:
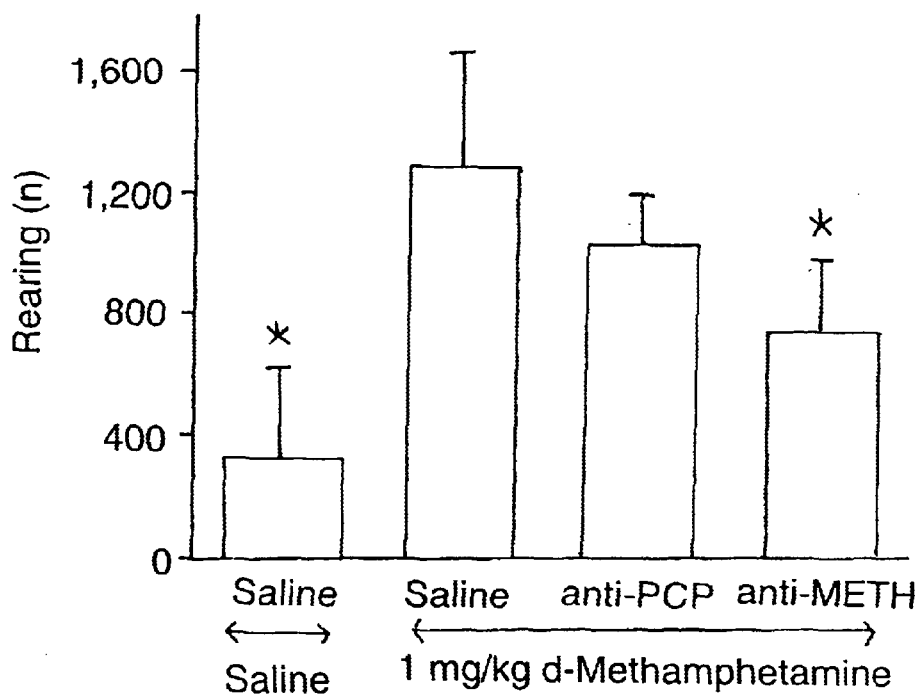
FIG. 8B shows the number of metampetamine-induced rearing events from 30 minutes after saline or d-methamphetamine administration until the end of the experiment, 4.5 hours later. At the 30 min the animals were treated with ether saline, anti-phencyclidine Fab or anti-d-methamphetamine Fab. *p<0.05 compared to a 1 mg/kg dose of methamphetamine followed by the saline control treatment.

Based on the distance traveled parameter, the duration of action of methamphetamine-induced effects following a 1 mg/kg iv dose was about two hours (116±17 min). After treatment with anti-PCP Fab the duration of activity was 111±10 min. After treatment with anti-methamphetamine Fab the duration of activity was 75±22 min. Both the distance traveled (FIG. 8A) and the number of rearing events (FIG. 8B) were significantly different from the behaviors produced by saline followed by methamphetamine administration ($p<0.05$). The anti-PCP Fab treatment produced some mild reductions in methamphetamine-induced locomotor activity, which were similar to the mild reductions in behavior we have found in other experiments in which polyclonal non-specific antibody is used to treat PCP-induced locomotor activity. As a percentage of the control saline treatment, the monoclonal anti-methamphetamine Fab produced a 55% decrease in the distance traveled (see FIG. 8A). The number of rearing events (see FIG. 8B) and the time spent moving (results not shown) were also decreased by 55% and 60%, respectively.

Since the monoclonal antibody used for these studies did not significantly bind to d-amphetamine (a psychoactive metabolite present at very high levels in the rat, but at significantly lower levels in the human) and it was a low affinity antibody (about 250 nM), the therapeutic potential for antibody based medications for overdose are quite significant. This is especially important since no therapies currently exist.

With the use of improved hapten design (see Example 2) and production of antibodies with significantly lower Kd values (e.g., <30 nM), this invention should provide a significant breakthrough in treatment of overdose due to d-amphetamine-like drugs. This is supported by experiments using a monoclonal antibody 6H4 that has a Kd of 11 nM, which is approximately 25× lower Kd value than the 250 Kd monoclonal antibody used in the previous studies. This new antibody is highly specific for (+)METH and (+)MDMA, with little to no cross reactivity with (+)AMP or (+)MDA, or the minus isomers of these chemicals. The following experimental data show the feasibility of using this or other monoclonal antibodies in two different preclinical scenarios: drug overdose and the use of pretreatment with monoclonal antibody therapy to block the pharmacological effects of methamphetamine abuse.

EXAMPLE 16

Use of an 11 nM Kd anti-(+)meth Monoclonal IgG Antibody to Reverse Drug Overdose Rats (n=6/group) were administered i.v. (+)methamphetamine (1.0 mg/kg) 3 days apart on two occasions to stabilize locomotor responses and to minimize sensitization. Then 1.0 mg/kg of (+)methamphetamine was administered i.v., and 30 min later (when effects were maximal) a dose of 367 mg/kg of anti-methamphetamine monoclonal antibody was administered. This dose was equimolar (in binding sites) to the rat body burden of (+)methamphetamine.

Figure 9A:
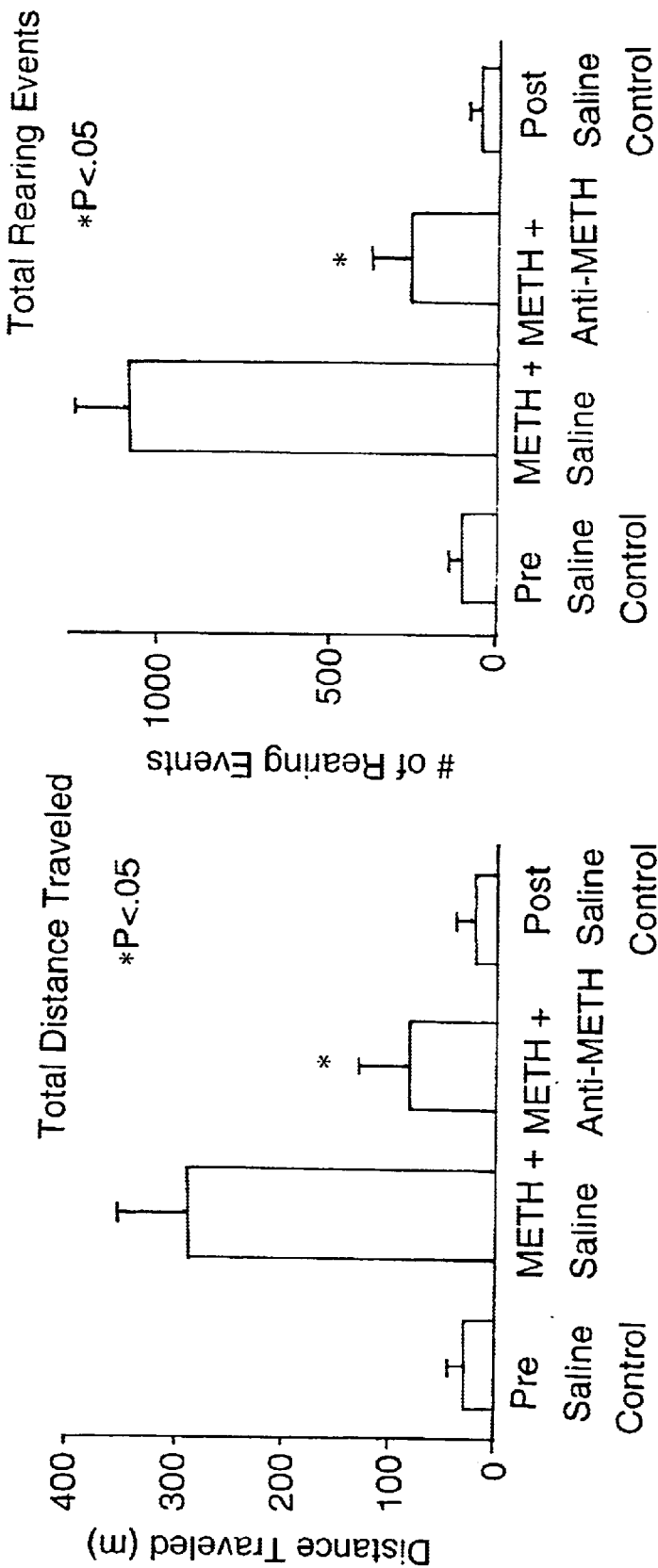
As shown in FIG. 9A, the anti-(+) methamphetamine monoclonal antibody (administered 30 minutes after methamphetamine) significantly (P<0.05) reduced (+)methamphetamine induced effects by 72% for distance traveled (left) and by 76% for rearing events (right).

As shown in FIG. 9A, the anti-(+) methamphetamine monoclonal antibody significantly ($P<0.05$) reduced (+)methamphetamine induced effects by 72% for distance traveled (left) and by 76% for rearing events (right). The monoclonal antibody significantly shortened the duration of action of (+)methamphetamine from 112 to 32 min. Saline control treatments, conducted before and after the experimental protocol showed that baseline activity was stable over an extended period.

EXAMPLE 17

Pretreatment with an 11 nM Kd anti-(+) Methamphetamine Monoclonal IgG Antibody to Reduce the Effects of (+)methamphetamine in an Rat Model of Drug Abuse Rats (n=7/group) were administered a dose of 502 mg/kg of anti-methamphetamine monoclonal antibody on day 1.

Figure 9B:
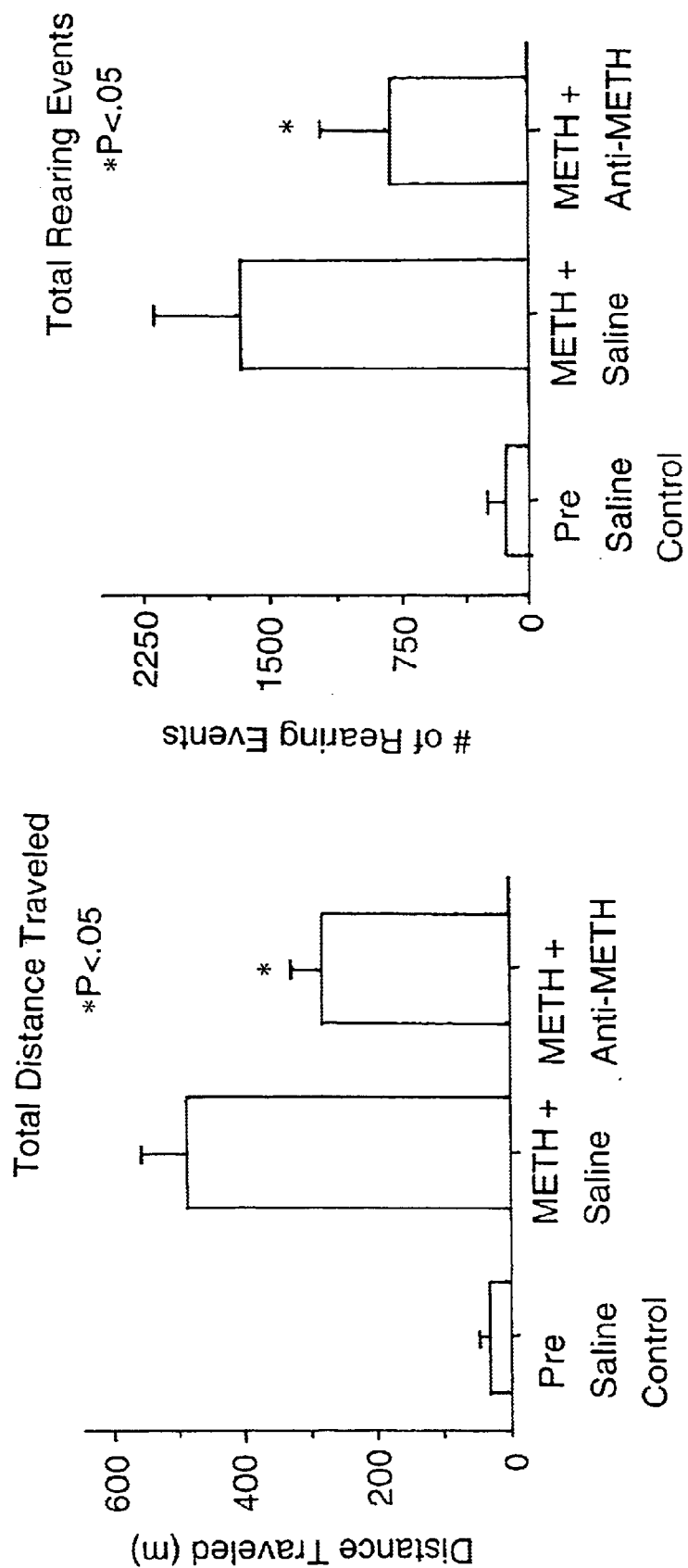
As shown in FIG. 9B, (administered the day a 1 mg/kg methamphetamine challenge dose) the anti-(+) methamphetamine monoclonal antibody significantly (P<0.05) reduced (+)methamphetamine induced effects by 42% for distance traveled (left) and by 51% for rearing events (right).

The following day they were administered i.v. (+)methamphetamine (1.0 mg/kg) 3 days apart on two occasions to stabilize locomotor responses and to minimize sensitization. Then 1.0 mg/kg of (+)methamphetamine was administered i.v. This dose was equimolar (in binding sites) to a 1 mg/kg dose of (+)methamphetamine. As shown in FIG. 9B, the anti-(+) methamphetamine monoclonal antibody significantly ($P<0.05$) reduced (+)methamphetamine induced effects by 42% for distance traveled (left) and by 51% for rearing events (right). The monoclonal antibody significantly shortened the duration of action of (+)methamphetamine from about 160 to 80 min. Saline control treatments conducted before and after the experimental protocol showed that baseline activity was stable over an extended period.

EXAMPLE 18

Impact of Anti-D-Methamphetamine Therapy on Drug Self-Administration and Drug Discrimination as a Measure of Treating Long-Term Addiction Drug self-administration is generally considered to be a measure of the reinforcing properties of a drug and is widely used to measure the addiction liability of different drugs. Before self-administration of methamphetamine by a rat can be used as a model of the pharmacotherapeutic effects of anti-methamphetamine IgG, it is necessary to develop a suitable methamphetamine self-administration model. Therefore, four rats with external carotid catheters were trained to respond on a lever for food. Once conditioned for this response, food was discontinued and each response on a lever in the cage produces an injection of 0.06 mg/kg d-methamphetamine. After several sessions under this schedule, the reinforcement schedule was changed to fixed-ratio 3, such that 3 responses are required to produce each injection of d-methamphetamine. The d-methamphetamine was available for two hours each day, after which the rat is returned to the home cage until the next session. Sessions were conducted 7 days a week. After responding for d-methamphetamine is stable, the pharmacotherapeutic effects of anti-methamphetamine IgG were tested. Conditioned rats were administered an anti-methamphetamine IgG and the next day the rat was given the opportunity to respond for d-methamphetamine injections. A significant increase in the number of responses during a session indicates that the antibody was blocking only some of the reinforcing properties of the d-methamphetamine, and the animal was surmounting the protective effects of the antibody. A significant decrease in the number of responses during a session indicates that the antibody is blocking the all or most of the reinforcing properties of the d-methamphetamine In the drug discrimination procedure, animals were trained to recognize the presence or absence of a training drug by differential reinforcement of responses in the presence or absence of the drug. Animals were trained to respond on one lever to obtain food if drug has been administered and on another lever if the drug vehicle has been administered. The only cue that the animal has as to which responses will be reinforced each day is the interceptive stimuli produced by the drug. Once the discrimination is established, other doses of the training drug or doses of other drugs are administered to determine if they produce interceptive stimuli that can substitute for those of the training drug.

to study the effectiveness of immunotherapy for d-methamphetamine abuse, pigeons were trained to discriminate among pentobarbital, morphine, d-amphetamine and saline using a 4-key discrimination procedure where responding on the correct key was reinforced with food delivery under a fixed-ratio schedule. d-Methamphetamine generalizes completely to the training drug d-amphetamine in these sessions.

To determine if the d-methamphetamine discriminative stimulus could be blocked with the anti-methamphetamine antibody, pigeons were administered the antibody intravenously approximately 14 hours before determination of a cumulative methamphetamine dose-response curve. The hapten used for the production of the monoclonal antibodies was similar in design to the para-4 hapten described in Example 6. This hapten design is known to generate highly selective antibodies for d-methamphetamine, which do not have significant cross-reactivity with d-amphetamine. Thus, in this pigeon model of drug discrimination the antibody will bind to d-methamphetamine, but it is not expected to blunt or block effects due to other drugs including d-amphetamine, pentobarbital and morphine (the drug discrimination test compounds) metabolite in the brain. Nevertheless, these studies provide the proof of concept that monoclonal anti-methamphetamine monoclonal antibody IgG can produce beneficial, long lasting and selective therapeutic effects for d-methamphetamine. Inability to correctly identify the drug and a subsequent shifting of the methamphetamine dose-response curve in the presence of antibody indicates blockage of the drug discriminative stimulus.

Figure 10:
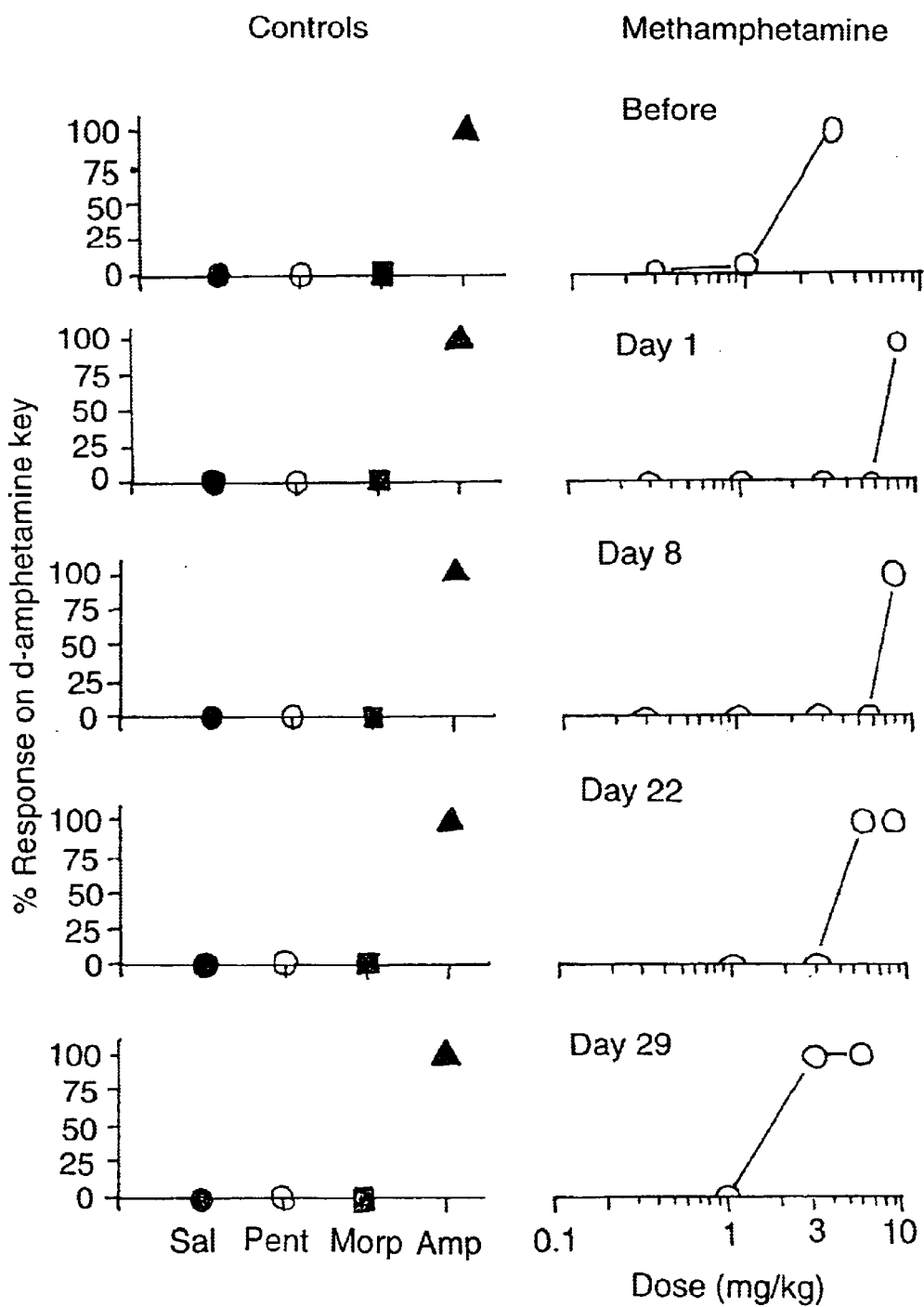
FIG. 10 shows the protective and long-acting protective effects of a monoclonal anti-methamphetamine antibody in a pigeon. This proof of concept study shows the selectivity of the antibody protective effects for d-methamphetamine and the long-lasted effects of a single dose of monoclonal antibody treatment.

As shown in FIG. 10, the anti-methamphetamine IgG produced a significant shift in the d-methamphetamine dose response curve for at least 22 days. Since this antibody did not have significant cross reactivity with d-amphetamine, pentobarbital or morphine, it offered no protection against the effects of these drugs. Thus, these studies provide proof of the potential for long lasting and selective effects in humans.

EXAMPLE 19

Effect of Antibody-Based Therapy on D-Methamphetamine Toxicity in Large Animal Model A battery of pharmacokinetics studies and behavioral tests are used to determine whether anti-d-methamphetamine Fab can reverse acute behavioral toxicity due to d-methamphetamine in large animals like large dogs (or primates). These data will help to determine the ability of anti-d-methamphetamine Fab to redistribute d-methamphetamine in a large animal model and help to scale-up the therapy to humans. d-Methamphetamine is administered to male dogs (or primates; n=6 per group, 3 males and 3 females) at 0.3 mg/kg or higher depending on results of preliminary d-methamphetamine dose-response studies. If needed for quantitation (see Example 5), a tracer dose of [$^3$H]-d-methamphetamine will also be administered. After the drug is fully distributed (e.g., 30–45 min), anti-d-methamphetamine Fab is administered at a 1.0 mol-eq dose to the amount of d-methamphetamine remaining in the dog (or primate) at 30 min. The exact timing and dosing depend on the outcome of the rat studies and the preliminary pharmacokinetic studies in dogs or primates. Plasma and urine d-methamphetamine pharmacokinetics are determined in each dog or primate as described above. The analytical methods for d-methamphetamine and anti-d-methamphetamine Fab are the same as those described in Example 5.

The same dogs (or primates) are used for the pharmacokinetic and behavioral studies for continuity. However, the success of the experiments is not dependent on using the same dog (or primate) for all experiments (n=6). For the behavioral experiments, d-methamphetamine are administered to dogs (or primates) at 0.3 mg/kg (or higher) followed 30–45 min later by a 0.1, 0.3, or 1.0 mol-eq dose of anti-d-methamphetamine Fab. The experiments are done in a pre-determined repeated-measures, mixed-sequence design. The same measures of behavior (and the EthoVision system) as described above are used for the studies of d-methamphetamine acute toxicity.

The following references were cited herein:
1. Collings, *Cable News Network* Feb. 13, 1996.
2. Cho, *Science* 249: 631–634 (1990).
3. Valentine and Owens, *J. Pharmacol. Exp. Ther.* 278: 717–724 (1996).
4. Owens et al., *J. Pharmacol. Exp. Ther.* 246: 472–478 (1988).
5. McClurkan et al., *J. Pharmacol. Exp. Ther.* 266: 1439–1445 (1993).
6. Minh-Tam et al., *Anal. Biochem.* 116: 402–407 (1981).
7. Laurenzana et al., *Drug Metab. Dispos.* 23: 271–278 (1995).
8. Goding, Monoclonal Antibodies: Principles and Practice. pp. 118–122, Academic Press, New York (1983).
9. Bazin-Redureau et al., *J. Pharm, Pharmacol.* In press.
10. Gibaldi and Perrier, Pharmacokinetics. Marcel Dekker, New York (1982).
11. Burchfield et al., *JAMA* 265(15): 1968–1973 (1991).
12. Doherty and Gratton, *Brain Res.* 715: 86–97 (1996).

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A monoclonal antibody that specifically recognizes a class or stimulant or hallucinogenic drug of abuse comprising d-methamphetamine, d-amphetamine, (+/−) 3,4-methylenedioxymethamphetamine, and (+/−) 3,4-methylenedioxyamphetamine, wherein said monoclonal antibody is generated by a hapten comprising (S)- or (R)-3-(5'-Carboxypentyloxy) methamphetamine hydrochloride.

2. The monoclonal antibody of claim 1, wherein said antibody is of murine origin.

3. The monoclonal antibody of claim 1, wherein said antibody is of human origin or contains portions of a human antibody.

4. An antibody fragment that specifically recognizes a class of stimulant or hallucinogenic drug of abuse comprising d-methamphetamine, d-amphetamine, (+/−) 3,4-methylenedioxymethamphetamine, and (+/−) 3,4-methylenedioxyamphetamine, wherein said antibody fragment is part of a monoclonal antibody generated by a hapten comprising (S)- or (R)-3-(5'-Carboxypentyloxy) methamphetamine hydrochloride.

5. The antibody fragment of claim 4, wherein said antibody fragment is of murine origin.

6. The antibody fragment of claim 4, wherein said antibody fragment is of human origin or contains portions of a human antibody.

7. A method of treating stimulant or hallucinogenic drug abuse and/or overdose, comprising the step of administering a pharmacological effective dose of the monoclonal antibody of claim 1 to an individual in need of such treatment.

8. The method of claim 7, wherein said stimulant or hallucinogenic drug is selected from the group consisting of d-methamphetamine, d-amphetamine, (+/−) 3,4-methylenedioxymethamphetamine, and (+/−) 3,4-methylenedioxyamphetamine.

9. A method of treating stimulant or hallucinogenic drug abuse and/or overdose, comprising the step of administering a pharmacological effective dose of the antibody fragment of claim 4 to an individual in need of such treatment.

10. The method of claim 9, wherein said stimulant or hallucinogenic drug is selected from the group consisting of d-methamphetamine, d-amphetamine, (+/−) 3,4-methylenedioxymethamphetamine, and (+/−) 3,4-methylenedioxyamphetamine.

\* \* \* \* \*